(12) United States Patent
Donaldson, IV

(10) Patent No.: US 11,504,326 B2
(45) Date of Patent: Nov. 22, 2022

(54) LIPID EMULSION THERAPY FOR TREATING ACUTE CANNABINOID INTOXICATION

(71) Applicant: Jack Donaldson, IV, Fort Lauderdale, FL (US)

(72) Inventor: Jack Donaldson, IV, Fort Lauderdale, FL (US)

( * ) Notice: Subject to any disclaimer, the term of this patent is extended or adjusted under 35 U.S.C. 154(b) by 0 days.

(21) Appl. No.: 16/795,019

(22) Filed: Feb. 19, 2020

(65) Prior Publication Data
US 2020/0261361 A1    Aug. 20, 2020

Related U.S. Application Data

(60) Provisional application No. 62/807,345, filed on Feb. 19, 2019.

(51) Int. Cl.
| | | |
|---|---|---|
| *A61K 9/107* | (2006.01) | |
| *A61K 9/00* | (2006.01) | |
| *A61K 31/23* | (2006.01) | |
| *A61K 31/231* | (2006.01) | |
| *A61K 31/685* | (2006.01) | |

(52) U.S. Cl.
CPC ............ *A61K 9/107* (2013.01); *A61K 9/0019* (2013.01); *A61K 9/0053* (2013.01); *A61K 31/23* (2013.01); *A61K 31/231* (2013.01); *A61K 31/685* (2013.01)

(58) Field of Classification Search
CPC ...................................................... A61K 9/107
See application file for complete search history.

(56) References Cited

U.S. PATENT DOCUMENTS 6,720,001 B2 *   4/2004   Chen .................... A61K 31/355
                                                    424/455

OTHER PUBLICATIONS

Alipour et al. Ment Health Clin, 2019, 9(2): 93-99.*

* cited by examiner

*Primary Examiner* — Rei Tsang Shiao
(74) *Attorney, Agent, or Firm* — David P. Lhota, Esq.; Lhota & Associates, P.A.

(57) ABSTRACT

A lipid emulsion composition including soybean oil, egg lecithin, glycerol and, or osmolality and method for treating acute cannabinoid intoxication or intoxication from other substances, such as alcohol or other drugs, by orally or intravenously administering this composition according to a predetermine protocol to treat patients experiencing acute cannabinoid intoxication or intoxication from other substances. The lipid emulsion composition could be administered to the intoxicated patient orally or intravenously. In some embodiments, the lipid emulsion composition includes soybean oil, egg yolk phospholipids, and glycerin.

4 Claims, No Drawings ized form that are especially attractive to children, such as those made in the form of gummy bears, brownies, lollipops, etc. Children may mistake these as conventional food treats and consume *cannabis* unknowingly. Also, small children are at higher risk of severe intoxication because of their smaller body size and weight. Because edible products often have very high amounts of marijuana, the symptoms of intoxication are more severe on a small child.

LIPID EMULSION THERAPY FOR TREATING ACUTE CANNABINOID INTOXICATION

CROSS-REFERENCE TO RELATED APPLICATION

This application claims the benefit of provisional patent application Ser. No. 62/807,345 filed Feb. 19, 2019.

STATEMENT REGARDING FEDERALLY SPONSORED RESEARCH OR DEVELOPMENT

N/A

FIELD OF THE INVENTION

The present invention relates to a lipid emulsion therapy formulation for treating cannabinoid intoxication, and in particular, to a liquid emulsion therapy formulation or composition and method for administering a liquid emulsion therapy formulation or composition to treat patients experiencing acute cannabinoid intoxication. The liquid emulsion therapy composition and method for administering same may be modified to treat patients with overdose incidents involving fentanyl, prescription pain relievers, heroin, cocaine, antidepressants, methamphetamine, acetaminophen, alcohol, diphenhydramine, sedatives, dextromethorphan, benzodiazepines and new diagnosis cannabinoid-hyperemesis-syndrome-marijuana.

BACKGROUND OF THE INVENTION

Marijuana has been used recreationally in the USA for several decades and its use is increasing because a growing number of states have decriminalized it and have its use legal for recreational purposes. Other states have made or are in the process of making its use for Medicinal purposes legal. In fact, Marijuana has been officially approved for Chemotherapy-induced nausea and vomiting, Epilepsy, Anorexia-Cachexia Syndrome (HIV), Glaucoma and Multiple Sclerosis. Its use has been proposed for a number of medical conditions including Anxiety, Depression, Insomnia, Migraine Headaches, selected Chronic Pain Syndromes, Arthritis, Parkinson Disease and Tourette syndrome. To that end, numerous THC-analogues are currently available for these potential therapeutic indications. As a consequence of the widespread increase in the use of Cannabinoid products, the potential for product toxicity and overdose are becoming more likely and therefore effective therapies to deal with those complications should be readily available.

With the ongoing liberalization of laws governing *cannabis* use, one of the public health impacts will be an increasing incidence of acute *cannabis* (marijuana) intoxication requiring medical attention (e.g. visits to the emergency room or calls to the regional poison control center). In addition to the decriminalization and legalization of *cannabis* use, other factors will exacerbate this increasing incidence of acute *cannabis* intoxication. One is the higher potency of today's *cannabis* products. In general, marijuana potency has increased over the past 15 years. Currently, the THC strength of recreational *cannabis* in Colorado can exceed 25%. See Bidwell et al, "A Novel Observational Method for Assessing Acute Responses to *Cannabis*: Preliminary Validation Using Legal Market Strains" (2018) *Cannabis* Cannabinoid Res. 3(1):35-44. Likewise, ingestible forms of *cannabis* (commonly referred to as infused edibles) often contain very high doses of tetrahydrocmannabinol. Naive users may be particularly vulnerable to severe intoxication from these high potency *cannabis* products.

Another reason for the rise in severe *cannabis* intoxication is that infused edible *cannabis* products are becoming more popular in the market. Edible forms of marijuana pose a special risk of unintentional ingestion by children. In fact, some edible products are made into a palatable and appetizing form that are especially attractive to children, such as those made in the form of gummy bears, brownies, lollipops, etc. Children may mistake these as conventional food treats and consume *cannabis* unknowingly. Also, small children are at higher risk of severe intoxication because of their smaller body size and weight. Because edible products often have very high amounts of marijuana, the symptoms of intoxication are more severe on a small child.

At the present time, the only reliable methods of managing Marijuana toxicity and overdose are largely supportive and include airway management, circulatory support, neurological monitoring and the use of selective drugs to treat specific signs and symptoms. Whereas, these techniques can be effective in the long run, it is becoming very desirable to develop a drug or series of drugs that may specially reverse the effects of Marijuana overdose in a manner similar to that of Naloxone (Narcan) reversing the Cardio-respiratory effects of Opioid Overdose. Colorado hit a record high 86 million visitors in 2017 has seen the increase of tourist that come to the state to abuse marijuana and overdose because they are not use to higher grades or understand the amount of THC in edibles. The Colorado Emergency Room has continually treated more patients overdosing on marijuana since approving the drug for recreational use in the state.

This concern has been confirmed by recent clinical case reports. To take one example, after legalization of recreational marijuana in Colorado, annual calls to the regional poison control center for pediatric marijuana exposure increased 34 percent, which was almost twice the rate for the rest of the United States. See Wang et al, "Unintentional Pediatric Exposures to Marijuana in Colorado, 2009-2015" (2016) JAMA Pediatrics, 170:e160971. Hospital visit rates at a large regional children's hospital system also increased significantly during the period of the study.

Thus, as the decriminalization and legalization of *cannabis* continues, and as it becomes more widely available and used, there is a need for a safe and effective treatment to rapidly reverse acute *cannabis* intoxication. It is known that THC is lipophilic so when ingested it rapidly binds to fatty structures in the brain and the rest of the central nervous system, kidneys and other fatty deposits in the body largely because of its high solubility in fatty tissues. It is that interaction that is mainly responsible for the neurological and psychomotor symptoms associated with THC toxicity. Intralipids, by virtue of their capacity to bind to the highly lipophilic THC, can reverse the toxic effects associated with marijuana toxicity. If there existed a natural formulation or composition and method for administering the same that could bind to the highly lipophilic THC on the fatty structures in the brain it could reverse the toxic effects associated with marijuana toxicity. As there are no known formulations or methods for reversing or treating acute cannabinoid intoxication, there exists a need for such a formulation or composition and method. It is, therefore, to the effective resolution of the aforementioned problems and shortcomings of the prior art that the present invention is directed. The instant invention addresses this unfulfilled need in the prior art by providing formulation/composition and method as contemplated by the instant invention disclosed.

SUMMARY OF THE INVENTION

In light of the foregoing, it is an object of the present invention to provide a formulation/composition and method of treating a patient having acute cannabinoid intoxication. The method comprises performing a mental status examination on the patient. The lipid emulsion composition includes soybean oil, egg lecithin, glycerol and, or osmolality which is administered to the intoxicated patient. In some embodiments, the lipid emulsion composition is administered intravenously. The intravenous administration may be performed in any suitable manner, such as bolus injection or steady infusion. In some embodiments, the lipid emulsion composition is orally administered.

In some embodiments, the lipid emulsion composition comprises soybean oil. In some embodiments, the lipid emulsion composition further comprises egg yolk phospholipids. In some embodiments, the lipid emulsion composition further comprises glycerin. In some embodiments, the lipid emulsion composition comprises neutral triglycerides; and in some cases, further comprises phospholipids; and in some cases, further comprises glycerin. Examples of fatty acid chains (that make up the triglycerides) include linoleic acid, oleic acid, palmitic acid, a-linolenic acid, and stearic acid. Examples of natural oil sources that contain such triglycerides include soybean oil, canola oil, and olive oil. Examples of phospholipids include phosphatidylcholine and phosphatidylethanolamine.

This invention may be particularly useful in pediatric patients. In some embodiments, the subject patient is younger than 13 years age; in some cases, younger than 11 years age; in some cases, younger than 9 years age. In some embodiments, the subject patient weighs less than 50 kg; in some cases, less than 45 kg; and in some cases, less than 40 kg. The instant invention provides a formulation or composition and method for reversing and treating debilitating neurological and psychomotor effects of marijuana or THC toxicity and may also be used or modified for use in treating patients with overdose incidents involving fentanyl, prescription pain relievers, heroin, cocaine, antidepressants, methamphetamine, acetaminophen, alcohol, diphenhydramine, sedatives, dextromethorphan, benzodiazepines and new diagnosis cannabinoid-hyperemesis-syndrome-marijuana.

In one embodiment, for a patient suffering with possible cannabinoid intoxication, the method of the instant invention includes accessing the patient for recent cannabinoid use or exposure, for example, by patient history, medical records, or witness reports; taking vital signs (blood pressure, pulse, body temperature, 02 saturation) and electrocardiography (ECG); securing intravenous line access; administering fluid resuscitation according to clinical judgement; performing physical examination, with particular attention to signs of recreational drug use; performing neurologic and mental status examination; performing intubation if necessary; performing rapid urine drug screen; drawing blood and order laboratory tests according to clinical judgement; administering 20% intralipid according to drug detoxification protocol; continue monitoring vital signs and performing repeat neurological and mental status examinations to assess for recovery from intoxication. In alternative embodiments, the instant invention may administer 10% or 30% intralipids for reversing or treating THC or marijuana toxicity.

The method may further comprise, during or after administering the lipid emulsion composition, repeating the mental status examination. As a result of the treatment, the subject patient may experience improvements in one or more of the various components of the mental status assessment. In some embodiments, the patient has improvement in behavior, such as eye contact (e.g. poor) or psychomotor activity (e.g. retardation). In some embodiments, the patient has improvement in speech, such as speech rate (e.g. increased/pressured, decreased/monosyllabic, latency); speech rhythm (articulation, prosody, dysarthria, monotone, slurred); or speech content (e.g. fluent, loquacious, paucity, impoverished).

In some embodiments, the patient has improvement in thought process, such as rate of thoughts, and how they flow and are connected. Normal thought process would be tight, logical and linear, coherent, and goal directed. Whereas abnormal thought process would be associations that are not clear, not organized, and not coherent. Examples of abnormal thought processes include those that are circumstantial, tangential, loose, flight of ideas, word salad, clanging, thought blocking. In some embodiments, the patient has improvement in cognition, such as level of consciousness, attention, and concentration (e.g. ability to focus, sustain, and appropriately shift mental attention), memory (immediate, short, and long term), or abstraction (e.g. proverb interpretation).

In accordance with these and other objects, which will become apparent hereinafter, the instant invention will now be described in the detailed description of the invention.

DETAILED DESCRIPTION OF THE INVENTION

This instant invention is a lipid emulsion composition 10 and method for administering the composition 100 to treat patients experiencing acute cannabinoid intoxication. Cannabinoids are a diverse class of chemical compounds that act on cannabinoid receptors in cells that alter neurotransmitter release in the brain. Ligands for these receptor proteins include the endocannabinoids (produced naturally in the body by animals), the phytocannabinoids (found in *cannabis* and some other plants), and synthetic cannabinoids (manufactured artificially). The most notable cannabinoid is the phytocannabinoid tetrahydrocannabinol (THC), the primary psychoactive compound in *cannabis*. Cannabidiol (CBD) is another major constituent of the *cannabis* plant. The liquid emulsion therapy composition and method for administering same may be modified to treat patients with overdose incidents involving fentanyl, prescription pain relievers, heroin, cocaine, antidepressants, methamphetamine, acetaminophen, alcohol, diphenhydramine, sedatives, dextromethorphan, benzodiazepines and new diagnosis cannabinoid-hyperemesis-syndrome-marijuana.

Pharmacokinetics. THC is a lipid soluble, highly protein-bound (95-99%) drug that has a volume of distribution of 2.5-3.5 L/kg. The pharmacokinetics of THC vary by route of administration. For inhaled marijuana, onset of psychoactive effects occurs rapidly with peak effects felt at 15-30 minutes and lasting up to four hours. These effects mirror plasma THC concentrations. Approximately 2-3 mg of inhaled THC is sufficient to produce drug effects in naïve user. Pulmonary bioavailability varies from 10-35% percent of an inhaled dose and is determined by the depth of inhalation, along with the duration of puffing and breath-holding.

Ingested marijuana has a delayed onset of effect that ranges from 30 minutes to three hours, with clinical effects lasting up to 12 hours. Orally administered *cannabis* has low bioavailability (5-20%) because of chemical degradation in gastric acid and substantial first-pass metabolism in the liver. In naive users, psychotropic effects occur with 5-20 mg of ingested THC.

*Cannabis* Toxicity. In recreational *cannabis* use, there is no clear demarcation between the dose that achieves effects desired by the user and the dose that produces noxious effects. Because of this lack of clarity in dosing, recreational *cannabis* use can often result in adverse effects. In adolescents and adults, inhaled doses of 2-3 mg of THC and ingested doses of 5-20 mg of THC impairs attention, concentration, short-term memory, and executive functioning. More severe adverse effects may occur at higher doses, such as nausea, postural hypotension, delirium, panic attacks, anxiety, and myoclonic jerking. Psychosis has also been associated with use of higher potency/concentrated *cannabis* products.

Toxicity in children most often occurs with ingestion of a highly concentrated *cannabis* food product. Estimated oral doses from 5-300 mg in children have caused a range of symptoms such as mild sleepiness, ataxia, behavior changes, excessive and purposeless motor activity of the extremities (hyperkinesis), coma, and respiratory depression with more severe intoxication correlated with higher estimated doses.

Clinical Manifestations. The clinical manifestations of acute *cannabis* intoxication vary according to age. In children, neurologic abnormalities are more prominent. At smaller doses, children may display sleepiness, euphoria, irritability, lethargy, and excessive and purposeless motor activity of the extremities (hyperkinesis). Vital signs may show sympathomimetic effects (e.g. tachycardia and hypertension), or bradycardia in patients with depressed mental status. Nausea, vomiting, conjunctival injection (red eye), nystagmus, ataxia, and slurred speech may also be present. Large overdoses may cause coma with apnea or depressed respirations.

In adolescents and adults, acute marijuana intoxication is often not the primary complaint. Patients who come to medical attention are more likely to complain of hyperemesis or behavioral problems (e.g. dysphoria or agitation) caused by adverse *cannabis* effects or medical emergencies (e.g. bronchospasm or pneumothorax) associated with *cannabis* inhalation. The physiologic signs of *cannabis* intoxication in adolescents and adults include: tachycardia; increased blood pressure; in the elderly, orthostatic hypotension; increased respiratory rate; conjunctival injection (red eye); dry mouth; increased appetite; nystagmus; ataxia; or slurred speech. In asthmatic patients, inhalation may induce acute asthma exacerbations or poor chronic symptom control.

*Cannabis* intoxication in adolescents and adults also results in neuropsychiatric effects that affect mood, perception, and thought content. There is typically a "high" feeling marked by euphoria and a decrease in anxiety, alertness, depression, and tension. However, first-time *cannabis* users, as well as anxious or psychologically vulnerable persons, may experience anxiety, dysphoria, and panic. Increased sociability usually occurs during intoxication, although dysphoric reactions may be accompanied by social withdrawal. Inexperienced users who ingest *cannabis* products may not be aware of the delayed onset of effect (up to three hours), which may induce them to continue to consume high potency products with an increased likelihood of dysphoria.

Lipid Emulsion Therapy. For this invention, a lipid emulsion composition is administered to the patients experiencing acute cannabinoid intoxication. Intravenous lipid emulsions have had a role in toxicology as an antidote to medication overdose or accidental exposure, in particular, as rescue from systemic toxicity brought on by local anesthetics. The lipid emulsion may work by a "lipid sink" mechanism of action. This "lipid sink" mechanism proposes that lipid-soluble drugs, such as local anesthetics, are absorbed into the lipid emulsion of the plasma and removed from tissues affected by toxicity. That is, infusing a large amount of lipids to the blood could move the lipid-soluble drugs away from the site of toxicity and dissolve it in the plasma, which would alleviate the toxic effects of the lipid-soluble drug. THC is a highly lipophilic (fat-soluble) compound and is likely to be drawn into this "lipid sink" created by the administered lipid emulsion treatment.

Lipid Emulsion Composition. Any suitable lipid emulsion composition may be used in this invention. One particular lipid emulsion product that could be used is Intralipid®. Intralipid is a fat emulsion containing soybean oil, egg yolk phospholipids, glycerin, and water. The emulsified fat particles are approximately 0.5 μm size. Because it is intended for intravenous infusion, Intralipid is sterile and buffered for pH range of 6.0 to 8.9. Soybean oil itself is a refined natural product that is a mixture of neutral triglycerides of predominantly unsaturated fatty acids. The neutral triglycerides have the following general structure:

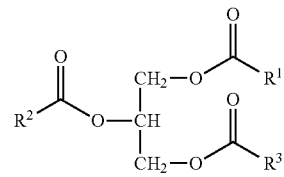

where R1, R2, and R3 are saturated and unsaturated fatty chains. The major constituent fatty acids are linoleic acid (44-62%), oleic acid (19-30%), palmitic acid (7-14%), a-linolenic acid (4-11%), and stearic acid (1.4-5.5%).

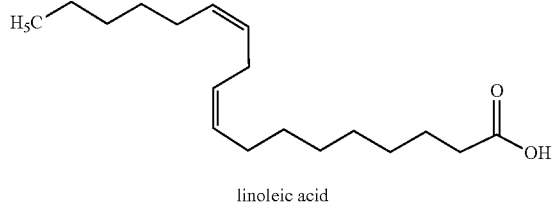

linoleic acid

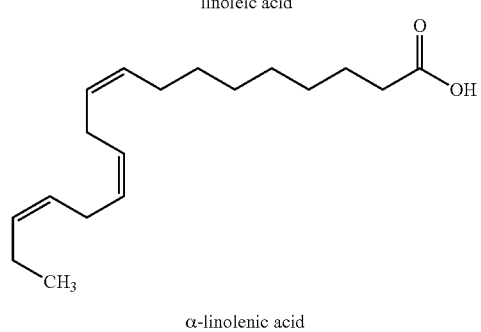

α-linolenic acid

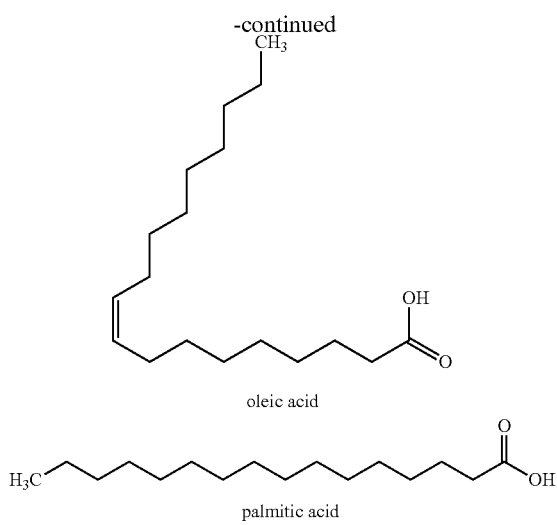

oleic acid palmitic acid

The purified egg phosphatides are a mixture of naturally occurring phospholipids isolated from egg yolk. These phospholipids have the following general structure:

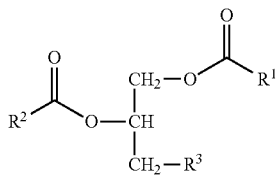

where R1 and R2 are saturated or unsaturated fatty chains. R3 is primarily either the choline or the ethanolamine ester of phosphoric acid.

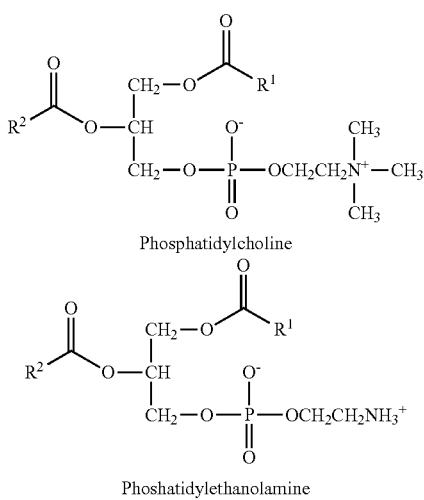

Phosphatidylcholine

Phoshatidylethanolamine

Intralipid is available in varying formulations. Intralipid 20% is a fat emulsion containing 20% soybean oil, 1.2% egg yolk phospholipids, 2.25% glycerin, and water. This 20% formulation has an osmolality of approximately 350 mOsmol/kg water (which represents 260 mOsmoL/L of emulsion). The composition of other formulations of Intralipid are provided in Table 1 below.

| | Content per 1000 ml | | |
| --- | --- | --- | --- |
| | Intralipid 10% | Intralipid 20% | Intralipid 30% |
| Soybean oil | 100 g (10 wt %) | 200 g (20 wt %) | 300 g (30 wt %) |
| Egg lecithin | 12 g | 12 g | 12 g |
| Glycerol | 22.0 g | 22.0 g | 22.0 g |
| Osmolality (mOsmol/kg water) | 300 | 350 | 310 |

Dosing. The lipid emulsion composition may be administered via any suitable route. Most typically, the lipid emulsion composition is administered by intravenous (IV) administration. But oral administration of the lipid emulsion composition may also be possible. See Tuzcu et al, "Oral intralipid emulsion use: a novel therapeutic approach to pancreatic β-cell injury caused by malathion toxicity in rats" (2014) Drug Chem Toxicol, 37(3):261-267. A variety of dosing formats are possible. For example, one possible dosing regimen for Intralipid 20% is to give 1.5 mL/kg as an initial bolus (which is about 100 mL in a typical 70 kg adult). If necessary, this bolus may be followed by a continuous infusion of 0.25 mL/kg/min over 60 minutes time. Additional boluses may be given or the infusion rate could be adjusted upwards as needed.

A clinical study that could be conducted to support the utility of the invention is as follows. For a patient presenting with possible cannabinoid intoxication, assess the patient for recent cannabinoid use or exposure, for example, by patient history, medical records, or witness reports. Take vital signs (blood pressure, pulse, body temperature, O2 saturation) and electrocardiography (ECG). Secure intravenous line access. Administer fluid resuscitation according to clinical judgment. Perform physical examination, with particular attention to signs of recreational drug use. Perform neurologic and mental status examination. Perform intubation if necessary. Perform rapid urine drug screen. Draw blood and order laboratory tests according to clinical judgement. Administer 20% Intralipid according to drug detoxification protocol. Continue monitoring vital signs. Perform repeat neurological and mental status examinations to assess for recovery from intoxication. The instant invention 10 may be used on or administered to adults, children and pets for reversal or treating of cannabinoid intoxication or other forms of intoxication mentioned herein.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A lipid emulsion composition and method for treating a patient having acute tetrahydrocannabinol intoxication with the lipid emulsion composition, comprising:
    assessing the patient for tetrahydrocannabinol intoxication;
    performing a mental status examination on the patient;
    administering a lipid emulsion composition to the patient, said lipid emulsion composition including soybean oil, lecithin, and glycerol; and
    repeating the mental status examination on the patient;
        wherein administration of the lipid emulsion composition results in an improvement in the patient's behavior, speech, thought process, or cognition as assessed by the patient's repeat mental status examination.

2. The method of claim 1, wherein the lipid emulsion composition further comprises:
   egg lecithin.

3. The method of claim 1, wherein the lipid emulsion composition having:
   osmolality.

4. The method of claim 1, wherein the lipid emulsion composition having:
   osmolality.

* * * * *